(12) United States Patent
Pourfallah (10) Patent No.: US 8,413,905 B2
(45) Date of Patent: Apr. 9, 2013

(54) PORTABLE PRESCRIPTION TRANSACTION PAYMENT DEVICE

(75) Inventor: Stacy Pourfallah, Oakland, CA (US)

(73) Assignee: Visa U.S.A. Inc., San Francisco, CA (US)

( * ) Notice: Subject to any disclaimer, the term of this patent is extended or adjusted under 35 U.S.C. 154(b) by 398 days.

(21) Appl. No.: 12/573,688

(22) Filed: Oct. 5, 2009

(65) Prior Publication Data
US 2011/0079648 A1 Apr. 7, 2011

(51) Int. Cl.
*G06K 19/06* (2006.01)
(52) U.S. Cl. .......................................... 235/492
(58) Field of Classification Search .................. 235/375, 235/383, 492; 705/2, 3
See application file for complete search history.

(56) References Cited

U.S. PATENT DOCUMENTS

| | | |
|---|---|---|
| 4,491,725 A | 1/1985 | Pritchard |
| 5,018,067 A | 5/1991 | Mohlenbrock et al. |
| 5,070,452 A | 12/1991 | Doyle, Jr. et al. |
| 5,175,416 A | 12/1992 | Mansvelt et al. |
| 5,235,507 A | 8/1993 | Sackler et al. |
| 5,301,105 A | 4/1994 | Cummings, Jr. |
| 5,324,077 A | 6/1994 | Kessler et al. |
| 5,335,278 A | 8/1994 | Matchett et al. |
| 5,550,734 A | 8/1996 | Tarter et al. |
| 5,628,530 A | 5/1997 | Thornton |
| 5,644,778 A | 7/1997 | Burks et al. |
| 5,710,578 A | 1/1998 | Beauregard et al. |
| 5,832,447 A | 11/1998 | Rieker et al. |
| 5,915,241 A | 6/1999 | Giannini |
| 5,965,860 A | 10/1999 | Oneda |
| 5,995,939 A | 11/1999 | Berman |
| 6,012,035 A | 1/2000 | Freeman, Jr. et al. |
| 6,044,352 A | 3/2000 | Deavers |
| 6,082,776 A | 7/2000 | Feinberg |
| 6,112,183 A | 8/2000 | Swanson et al. |

(Continued)

FOREIGN PATENT DOCUMENTS

| | | |
|---|---|---|
| JP | 2005124991 | 5/2005 |
| JP | 2005124991 A * | 5/2005 |

(Continued)

OTHER PUBLICATIONS

Companion Guide 835 Health Care Claim Payment/Advice, Convansys, Jun. 24, 2004 XP002564865 http://www.njelkids.com/UL/pdf/NJ_835v1_20040820-2.pdf.

(Continued)

*Primary Examiner* — Seung Lee
(74) *Attorney, Agent, or Firm* — Cooley LLP; Walter G. Hanchuk; Nathan W. Poulsen (57) ABSTRACT

A portable prescription sample transaction payment device has a substrate with a surface rendering corresponding to a prescription medical supply sample. Memory, in contact with the substrate, stores an identifier for the prescription medical supply sample, a quantity for the prescription medical supply sample, a dosage for the prescription medical supply sample, and an identifier for a patient. The memory also stores a pharmaceutical company account for a dispensing pharmacist to charge the cost of the prescription medical supply sample for payment to a dispensing pharmacist account to reimburse the dispensing pharmacist for the prescription medical supply sample. An image corresponding to the prescription medical supply sample is stored in the memory, as is an identifier for a prescribing medical practitioner prescribing the prescription medical supply sample to the patient.

28 Claims, 5 Drawing Sheets

U.S. PATENT DOCUMENTS

| | | | |
|---|---|---|---|
| 6,151,588 | A | 11/2000 | Tozzoli et al. |
| 6,208,973 | B1 | 3/2001 | Boyer et al. |
| 6,243,687 | B1 | 6/2001 | Powell |
| 6,332,133 | B1 | 12/2001 | Takayama |
| 6,343,271 | B1 | 1/2002 | Peterson et al. |
| 6,401,079 | B1 | 6/2002 | Kahn et al. |
| 6,529,884 | B1 | 3/2003 | Jakobsson |
| 6,629,081 | B1 | 9/2003 | Cornelius et al. |
| 6,850,901 | B1 | 2/2005 | Hunter et al. |
| 6,877,655 | B1 * | 4/2005 | Robertson et al. ............ 235/375 |
| 6,915,265 | B1 | 7/2005 | Johnson |
| 6,988,075 | B1 | 1/2006 | Hacker |
| 7,072,842 | B2 | 7/2006 | Provost et al. |
| 7,174,302 | B2 | 2/2007 | Patricelli et al. |
| 7,295,988 | B1 | 11/2007 | Reeves |
| 7,428,494 | B2 | 9/2008 | Hasan et al. |
| 7,752,096 | B2 | 7/2010 | Santalo |
| 7,769,599 | B2 | 8/2010 | Yanak |
| 7,792,688 | B2 | 9/2010 | Yanak |
| 7,866,548 | B2 | 1/2011 | Reed et al. |
| 7,996,260 | B1 | 8/2011 | Cunningham |
| 2001/0037295 | A1 | 11/2001 | Olsen |
| 2001/0053986 | A1 | 12/2001 | Dick |
| 2002/0002534 | A1 | 1/2002 | Davis et al. |
| 2002/0002536 | A1 | 1/2002 | Braco |
| 2002/0019808 | A1 | 2/2002 | Sharma |
| 2002/0032583 | A1 | 3/2002 | Joao |
| 2002/0128863 | A1 | 9/2002 | Richmond |
| 2002/0138309 | A1 | 9/2002 | Thomas |
| 2002/0147678 | A1 | 10/2002 | Drunsic |
| 2002/0152180 | A1 | 10/2002 | Turgeon |
| 2002/0198831 | A1 | 12/2002 | Patricelli et al. |
| 2003/0009355 | A1 | 1/2003 | Gupta |
| 2003/0040939 | A1 | 2/2003 | Tritch et al. |
| 2003/0046154 | A1 | 3/2003 | Larson |
| 2003/0055686 | A1 * | 3/2003 | Satoh et al. ........... 705/3 |
| 2003/0193185 | A1 | 10/2003 | Valley |
| 2003/0200118 | A1 | 10/2003 | Lee et al. |
| 2003/0212642 | A1 | 11/2003 | Weller et al. |
| 2003/0225693 | A1 | 12/2003 | Ballard et al. |
| 2004/0006490 | A1 | 1/2004 | Gingrich et al. |
| 2004/0039693 | A1 | 2/2004 | Nauman et al. |
| 2004/0054935 | A1 | 3/2004 | Holvey et al. |
| 2004/0103000 | A1 | 5/2004 | Owurowa |
| 2004/0111345 | A1 | 6/2004 | Chuang et al. |
| 2004/0117250 | A1 | 6/2004 | Lubow |
| 2004/0128201 | A1 | 7/2004 | Ofir et al. |
| 2004/0138999 | A1 | 7/2004 | Friedman et al. |
| 2004/0148203 | A1 | 7/2004 | Whitaker et al. |
| 2004/0172312 | A1 | 9/2004 | Selwanes et al. |
| 2004/0186746 | A1 | 9/2004 | Angst |
| 2004/0210520 | A1 | 10/2004 | Fitzgerald et al. |
| 2004/0225567 | A1 | 11/2004 | Mitchell et al. |
| 2004/0254816 | A1 | 12/2004 | Myers |
| 2005/0010448 | A1 | 1/2005 | Mattera |
| 2005/0015280 | A1 | 1/2005 | Gabel et al. |
| 2005/0033609 | A1 | 2/2005 | Yang |
| 2005/0038675 | A1 | 2/2005 | Siekman et al. |
| 2005/0065819 | A1 | 3/2005 | Schultz |
| 2005/0065824 | A1 | 3/2005 | Kohan |
| 2005/0071194 | A1 | 3/2005 | Bormann et al. |
| 2005/0119918 | A1 | 6/2005 | Berliner |
| 2005/0182721 | A1 | 8/2005 | Weintraub |
| 2005/0187790 | A1 | 8/2005 | Lapsker |
| 2005/0187794 | A1 | 8/2005 | Kimak |
| 2005/0209893 | A1 | 9/2005 | Nahra et al. |
| 2005/0211764 | A1 | 9/2005 | Barcelou |
| 2005/0246292 | A1 | 11/2005 | Sarcanin |
| 2005/0273387 | A1 | 12/2005 | Previdi |
| 2005/0288964 | A1 | 12/2005 | Lutzen et al. |
| 2006/0010007 | A1 | 1/2006 | Denman et al. |
| 2006/0106645 | A1 | 5/2006 | Bergelson et al. |
| 2006/0106646 | A1 | 5/2006 | Squilla et al. |
| 2006/0111943 | A1 | 5/2006 | Wu |
| 2006/0129427 | A1 | 6/2006 | Wennberg |
| 2006/0129435 | A1 | 6/2006 | Smitherman et al. |
| 2006/0136270 | A1 | 6/2006 | Morgan |
| 2006/0149529 | A1 | 7/2006 | Nguyen et al. |
| 2006/0149603 | A1 | 7/2006 | Patterson et al. |
| 2006/0149670 | A1 | 7/2006 | Nguyen et al. |
| 2006/0161456 | A1 | 7/2006 | Baker et al. |
| 2006/0173712 | A1 | 8/2006 | Joubert |
| 2006/0184455 | A1 | 8/2006 | Meyer |
| 2006/0206361 | A1 | 9/2006 | Logan |
| 2006/0224417 | A1 | 10/2006 | Werner |
| 2006/0229911 | A1 | 10/2006 | Gropper et al. |
| 2006/0235761 | A1 | 10/2006 | Johnson |
| 2007/0005403 | A1 | 1/2007 | Kennedy |
| 2007/0027715 | A1 | 2/2007 | Gropper et al. |
| 2007/0061169 | A1 | 3/2007 | Lorsch |
| 2007/0106607 | A1 | 5/2007 | Seib et al. |
| 2007/0125844 | A1 | 6/2007 | Libin et al. |
| 2007/0143215 | A1 | 6/2007 | Willems |
| 2008/0010096 | A1 | 1/2008 | Patterson et al. |
| 2008/0071646 | A1 | 3/2008 | Hodson et al. |
| 2008/0147518 | A1 | 6/2008 | Sultan et al. |
| 2008/0177574 | A1 | 7/2008 | Gonzalez et al. |
| 2008/0281733 | A1 | 11/2008 | Kubo et al. |
| 2008/0306761 | A1 | 12/2008 | George |
| 2009/0006203 | A1 | 1/2009 | Fordyce et al. |
| 2009/0048871 | A1 | 2/2009 | Skomra |
| 2009/0079182 | A1 | 3/2009 | Dold |
| 2009/0326977 | A1 | 12/2009 | Cullen |
| 2010/0010901 | A1 | 1/2010 | Marshall et al. |
| 2010/0010909 | A1 | 1/2010 | Marshall |
| 2010/0162171 | A1 * | 6/2010 | Felt et al. ..................... 715/835 |
| 2010/0312631 | A1 | 12/2010 | Cervenka |
| 2010/0312635 | A1 | 12/2010 | Cervenka |

FOREIGN PATENT DOCUMENTS

| | | |
|---|---|---|
| JP | 2008545210 | 12/2008 |
| KR | 1020040028017 | 4/2004 |
| KR | 1020050099707 | 10/2005 |
| KR | 1020050094938 | 7/2006 |
| KR | 1020070041183 | 4/2007 |
| WO | WO99/22330 | 5/1999 |
| WO | WO01/06468 | 1/2001 |
| WO | WO03/073353 | 9/2003 |
| WO | WO2006/074285 | 7/2006 |

OTHER PUBLICATIONS

Hammond, W Edward and Cimino, James "Standards in Medical Informatics: Computer Applications in Health Care and Biomedicine," 2000 Springer, NY XP002564866, pp. 226-276.

Classen, David et al.; "the Patient safety Insitute demonstration Project: A Model for Implementing a Local Health information Infrastructure"; 2004, Journal of Healthcare Information Management, vol. 19, No. 4, pp. 75-86.

"Patient Safety Institute: Economic Value of a Community Clinical Information Sharing Network, Part 1: Value to Payers (Private, Medicare, Medicaid and self-Insured Employers) and the Uninsured"; 2004, White Paper prepared by Emerging Practives First consulting Group, 18 pages.

"Visa Introduces Next Generation B2B payment Service" downloaded on www.corporate.visa.com/md/nr/press136.jsp, Feb. 2, 2007, pp. 1-3.

"Visa USA Small Business & merchants, Visa ePay—How it Works" downloaded on www.usa.visa.com/business/accepting_visa/payment_technologies/epay_how_it_works.html, Feb. 2, 2007, p. 1.

"Visa USA Small Business & Merchants, Visa epay-Participating Financial Institutes" downloaded on www.usa.visa.com/business/accepting_visa/payment_technologies/epay_fi.html, at Feb. 2, 2007, p. 1.

"Visa ePay" downloaded on www.usa.visa.com/business/accepting_visa/payment_technologies/epay.html, Feb. 2, 2007, p. 1.

"Welcome to American Express Healthpay Plus Works, What is Pay Plus" downloaded on www.152.americanexpress.com/entcampweb/payment_technologies/epay_how_it_works.jsp, Feb. 2, 2007, pp. 1-2.

"Visa USA Small Business & marchants, Visa ePay-Credit counseling Automation" downloaded on www.usa.visa.com/business/accepting_visa/payment_technologies/epay_credit_counseling.html, Feb. 2, 2007, pp. 1-3.

"Visa Introduces Next Generation B2Bpayment service" downloaded on www.sellitontheweb.com/ezine/news0569.shtml, Feb. 2, 2007, pp. 1-4.

"welcome to American Express Healthpay Plus(SM)", What is HealthPay Plus downloaded on www.152.americanexpress.com/entcampweb/whatishealthpayplus.jsp at Feb. 2, 2007, pp. 1-3.

Supplementary European Search Report for EP 06717481.

International Search Report for PCT/US2006/00288.

Supplementary European Search Report for EP 06717470.

International Search Report for PCT/US2006/00274.

International Search Report for PCT/US2007/84179.

International Search Report for PCT/US2009/066847.

International Search Report for PCT/US2009/049203.

Search Report EIC 3600, Aug. 20, 2009 for U.S. Appl. No. 11/230,761.

Supplementary European Search Report for EP 06717482.

International Search Report for PCT/US2010/051355.

International Search Report for PCT/US2010/045500.

International Search Report for PCT/US2010/045445.

International Search Report for PCT/US2007/70780.

Supplementary European Search Report for European Patent Application EP 07798894.

International Search Report for PCT/US2007/71797.

Supplementary European Search Report for EP 08771445.7.

International Search Report for PCT/US2008/67460.

International Search Report for PCT/US2007/74862.

Recal Introduces WebSentry Reducing the Risk of Fraud for Internet Transactions; WebSentry Offers System Integrators Cost Effective Set Compliance for E-Commerce—Canadian Corporation News May 26, 1999.

Final Office Action dated Jun. 28, 2012 in Co-pending Related U.S. Appl. No. 12/573,817.

Final Office Action dated Jun. 28, 2012 in Co-pending Related U.S. Appl. No. 12/573,833.

Non-Final Office Action dated Jun. 8, 2012 in Co-pending Related U.S. Appl. No. 12/573,838.

Notice of Allowance dated Apr. 6, 2012 in Co-pending Related U.S. Appl. No. 12/573,846.

Non-Final Office Action dated Dec. 8, 2011 in Co-pending Related U.S. Appl. No. 12/573,817.

Non-Final Office Action dated Dec. 1, 2011 in Co-pending Related U.S. Appl. No. 12/573,833.

* cited by examiner

PORTABLE PRESCRIPTION TRANSACTION PAYMENT DEVICE

CROSS-REFERENCE TO RELATED APPLICATIONS

The case is filed concurrently with U.S. patent application Ser. No. 12/573,817 on Oct. 5, 2009, by Stacy Pourfallah, titled "Portable Consumer Transaction Payment Device Bearing Sponsored Free Sample," with U.S. patent application Ser. No. 12/573,833 on Oct. 5, 2009, by Stacy Pourfallah, titled "Portable Consumer Transaction Payment Device Bearing Sample Prescription," with U.S. patent application Ser. No. 12/573,838 on Oct. 5, 2009, by Stacy Pourfallah, titled "Free Sample Account Transaction Payment Card Kiosk," and with U.S. patent application Ser. No. 12/573,846 on Oct. 5, 2009, by Stacy Pourfallah, titled "Prescription Sample Transaction Payment Card," each of which is incorporated herein by reference.

FIELD

The present invention relates generally to the distribution of samples, and more particularly with the distribution of pharmaceutical samples, and most particularly to a sample transaction payment card that can be exchanged by a patient at a pharmacy dispensing the sample of the prescribed medical supply to the patient, the sample transaction payment card being associated with an account of a third party who is financially response for the cost of the prescribed medical supply sample.

BACKGROUND

When a patient sees a healthcare provider for an ailment, often the patient is provided samples of pharmaceutical products to try. This may be done when the healthcare provider is unsure which medication will alleviate the patient's symptoms or illness, or when a prescription is very expensive. However, this form of distribution can be dangerous. The healthcare provider may accidentally provide the wrong sample to the patient, might not keep accurate records of what samples were given, or may not be aware of possible interactions with medications the patient has been prescribed by other providers.

Additionally, the distribution of sample pharmaceutical products by healthcare providers is costly. Pharmaceutical companies must send the sample drugs to representatives, who are then paid to distribute the samples to local healthcare providers. These samples must be individually packaged, often with expensive safety features and elaborate advertisements. Further, the pharmaceutical companies must cover the cost of the samples themselves regardless of whether the healthcare provider ever actually distributes the samples. All of this adds to the soaring prices of medications.

Thus, there is a need for a system that allows healthcare providers to provide patients with access to sample medications within a more controlled environment, such as a pharmacy. Further, there is a need to reduce medication and medical supply costs by removing the expense of representatives and individual sample packaging.

SUMMARY

In one implementation, a portable prescription sample transaction payment device is provided with memory, embedded in a substrate, and having information stored in the memory. The substrate can have a surface with an image of a representation of the information in the memory. The image can be read by being scanned by a scanner at a Point of Service terminal. The information includes an identifier, quantity, and dosage for each of a plurality of prescription medical supply samples prescribed by a prescribing medical practitioner to a patient. The information can also include one or more non-sample prescription medical supplies prescribed by a corresponding prescribing medical practitioner to the patient. The information in the memory can also include an image of each prescription for the patient that was prescribed by the corresponding prescribing medical practitioner. For each prescription medical supply sample, a pharmaceutical company account is included in the information in the memory. The pharmaceutical company account can be used for a dispensing pharmacist to charge the cost of the prescription medical supply sample for payment to a dispensing pharmacist account to reimburse the dispensing pharmacist for the prescription medical supply sample. Also included in the information in the memory is an identifier to correlate which prescription for the patient was prescribed by which prescribing medical practitioner. A device or mechanism is provided by which the information in the memory can be accessed.

The foregoing advantages will appear in the detailed description that follows. In the description, reference is made to the accompanying drawings.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION

The present discussion considers a sample of a prescription medical supply that can be prescribed to a patient by a healthcare provider's use of a portable prescription transaction payment device, such as may have the form factor of a transaction payment card. Such a sample transaction payment card can be exchanged by the patient with a pharmacist who will dispense the sample of the prescription medical supply to the patient. In the present context, an account for the payment of a sample attributable to an electronic voucher is issued by an issuer to a third-party sponsor of the electronic voucher and credited with funds submitted by the third-party. The funds on deposit in the account are for reimbursement of the distribution of the sample by the dispensing pharmacist upon the presentation by the patient of the sample transaction payment card having the electronic voucher stored thereon. The sample transaction payment card is provided to the patient by a prescribing healthcare provider and has information stored therein for at least one electronic voucher.

Figure 1:
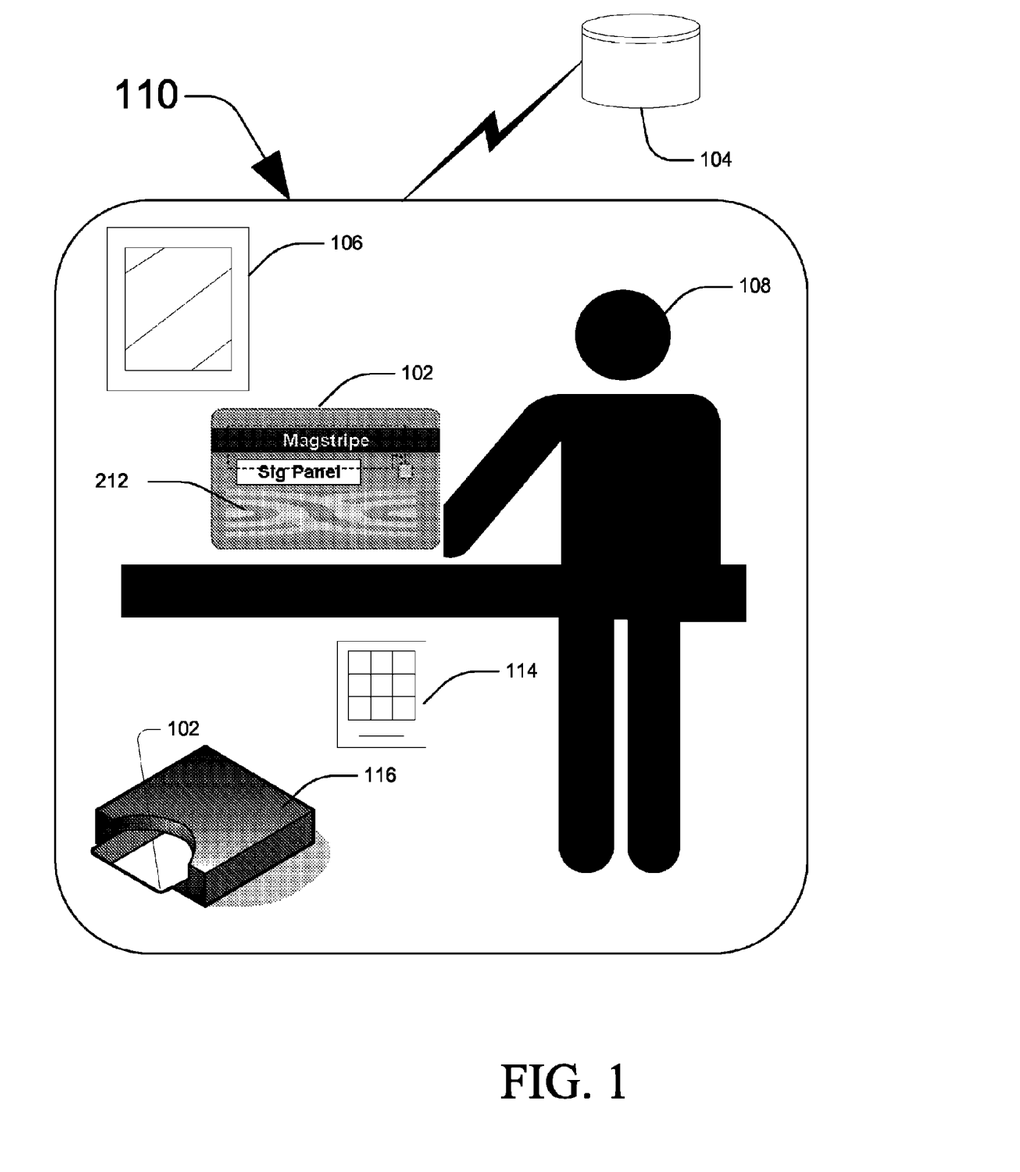
FIG. 1 depicts a block diagram of an exemplary method of a healthcare provider using a card processor system to associate a sample transaction payment card with an electronic voucher.

Turning now to FIG. 1, an exemplary block diagram is presented of an environment 110 of a healthcare provider using a card processor system to associate a sample transaction payment card with an electronic voucher, where the sample transaction payment card may be used by the patient for a sample medical supply prescribed by the healthcare provider to be dispensed to the patient by a pharmacist. Although the implementation is discussed in regards to a substantially planar laminated card, one skilled in the art will recognize that other forms of transaction payment tokens could be used.

Although the present application is primarily concerned with prescription medication, one of ordinary skill in the art will understand that the samples may be of prescription medical supplies, such as by way of example and not limitation, syringes or home medical supplies covered by health insurance. Furthermore, the samples may be of over-the-counter (OTC) medications or medical supplies, such as by way of example and not limitation, aspirin, antiseptics, bandages, creams, or salves.

Further, one of ordinary skill in the art will realize that, in the present discussion, "healthcare provider" is intended to include doctors, nurse practitioners, veterinarians, dentists, psychiatrists, veterinarians, and any other prescriber. Additionally, wherein the sample is for an OTC medication or medical supply, "healthcare provider" may include chiropractors, homeopathic therapists, acupuncturists, physical therapists, or any other provider of health-related services. Also, it will be understood that a patient of a healthcare provider could act through an agent to perform acts described herein.

In certain implementations, a card processor system is connected to a database 104. The card processor system, for instance, can create, from a blank transaction payment card, a prescription medical supply sample transaction payment card that is encoded with information to facilitate a transaction with a dispensing pharmacist for a patient to received the sample at substantially no cost. In certain implementations, database 104 is a database of electronic vouchers for free samples which healthcare provider 108 may distribute to patents. In one implementation, a third-party offering, and willing to pay for, the distribution of at least one sample using an electronic voucher has access to the database and may send to and receive from the database information such as the number of electronic vouchers used, the number of electronic vouchers remaining, alternatives to a given sample, medications commonly prescribed with a given sample and the availability of such medications, or any other relevant information.

In certain implementations, database 104 is connected to a network accessible by a computer used by healthcare provider 108. In such implementations, the network may be a Local Area Network (LAN), Wide Area Network (WAN), Personal Area Network (PAN), Virtual Private Network (VPN), Storage Area Network (WAN), Global Area Network (GAN), Internetwork, or combination thereof. In such implementations, the computer may connect to the network using wireless communications, optical fiber, Ethernet, ITU-T G.hn, or similar technology, or a combination thereof. In such implementations, the computer may include a network card, network adapter, or network interface controller (NIC). In other implementations, the computer may include other types of hardware capable of connecting to and communicating with a network.

In certain implementations, database 104 is provided by a web service in communication with a website. In such implementations, healthcare provider 108 browses, using a web browser of a web-enabled computer, to the website to select an electronic voucher from database 104.

In certain implementations, database 104 also includes information relating to each electronic voucher stored therein. In such implementations, database 104 may include an identifier for the free sample and an account identifier of the third-party sponsor of the electronic voucher. In certain implementations, the account of the third-party sponsor is a regulated account that's use is limited to payments to healthcare providers. In certain implementations, the third-party account is a revolving credit account, a debit account, or a prepaid account. In certain implementations, the third-party account is a Flexible Savings Account (FSA), a Health Savings Account (HAS), or a Health Reimbursement Account (HRA).

In certain implementations, database 104 includes information also regarding a merchant. In such an implementation, the electronic voucher may only be valid for use with a particular compounding pharmacy or drug store. In other implementations, the information includes the prescription date or an expiration date, after which the electronic voucher is no longer valid. In yet other implementations, the information includes the number of samples eligible for distribution using the electronic voucher. By way of example and not limitation, the electronic voucher may be valid for three (3) sample-sized tubes of a prescription topical cream. In other implementations, the database 104 includes information regarding an expiration date, after which the electronic voucher is no longer valid.

In certain implementations, database 104 includes advertisements and/or educational or safety information capable of being printed by a merchant Point Of Service terminal (POS), (i.e., a cash register) when the sample transaction payment card bearing the electronic voucher is presented to a pharmacist. In certain implementations, a specific advertisement is selected by healthcare provider 108 to be associated with the sample transaction payment card. In certain implementations, the advertisements are pre-associated with the electronic vouchers. In certain implementations, the advertisement may be an image. In certain implementations, the advertisement may be for a type of good or service, which may or may not be related to the free prescription sample. In certain implementations, the advertisement may be for the pharmacist providing the free sample or for the third-party sponsor. In certain implementations, the advertisement is of a different good or service provided by healthcare provider 108, the pharmacist, or by the third-party sponsor. In certain implementations, the advertisement is for a merchant, or a good or service provided by a merchant, whose retail location is near healthcare provider 108 or the pharmacist.

In some implementations, database 104 includes information regarding a coupon for a free or discounted item. The coupon may be issued by the sponsor of the electronic voucher. In other implementations, healthcare provider 108 may select a coupon from multiple coupons available in database 104. In yet other implementations, database 104 may automatically associate a coupon with sample transaction payment card 102. The association may be based upon the medications being prescribed, the diagnosis of the patient, or any other criteria. The coupon may be for discounts on prescription medication or over-the-counter items, such as, for example, cough syrups, bandages, or herbal teas. In one implementation the coupon expires with the use of the consumer payment device to obtain the sample associated with the electronic voucher, the discount only being redeemable at the time medication is dispensed. In other implementations, the coupon may be redeemable at a later time.

In certain implementations, the identifier of the free sample corresponds to a type of good or service. In certain implementations, the identifier is an image capable of being displayed or printed by a merchant POS. In certain implementations, the identifier of the free sample is a Stock Keeping Unit (SKU). In certain implementations, the identifier of the free sample is a Universal Product Code (UPC). In certain implementations, the identifier is of a trademark associated with the product being distributed as a sample, the trade name of the wholesaler of the product, or the trade name of the manufacturer of the product. In certain implementations, the identifier is for an active ingredient of the product being distributed as a free sample. In certain implementations, the identifier is a National Drug Code (NDC).

The card processor system, in some implementations, may include a user interface 106 capable of presenting healthcare provider 108 with a selection of electronic vouchers available for distribution. The user interface 106 may be a touch screen, a digital electronic display with an input device, a projector with an input device, a monitor with an input device, any combination of the foregoing, or any other device for the presentation of information.

Healthcare provider 108 may select an electronic voucher using input device 114. Input device 114 may be a key pad, a touch screen, a pointing device, an audio input device, a video input device, any combination of the foregoing, or other hardware capable of receiving and transforming data for use by the device.

Card read-write device 116 may then be used to associate the selected electronic vouchers with sample transaction payment card 102. In certain implementations, prior to association, sample transaction payment card 102 is a blank card. In certain implementations, sample transaction payment card 102 is provided by the third-party sponsor of the electronic voucher. In other implementations, sample transaction payment card 102 is provided by healthcare provider 108. In yet other implementations, sample transaction payment card 102 is provided by any other entity with an interest in the distribution of samples via electronic vouchers. Additionally, in certain implementations sample transaction payment card 102 is a one-time use card, being deactivated after it is redeemed for a sample from a merchant. In other implementations, sample transaction payment card 102 is capable of being used multiple times for multiple samples provided at a single or multiple merchant locations. In yet other implementations, sample transaction payment card 102 is a portable consumer device associated with a financial account that belongs to the patient card holder and may be capable of being used to conduct transactions for goods or services with various merchants.

Card read-write device 116 stores information relating to the electronic voucher selected by healthcare provider 108 on sample transaction payment card 102, including the account identifier associated with an account of the third-party sponsor of the electronic voucher.

In certain implementations, the electronic voucher may be for a sample made by a particular manufacturer. In such an implementation, the information may further include an identifier for the manufacturer. In certain implementations, the electronic voucher may be for a particular type of sample made by any manufacturer. In such an implementation, the information may further include an identifier for an acceptable generic alternative to the name-brand sample.

In certain implementations, the electronic voucher may be for a sample of an OTC medication or medical supply, such as, by way of example and not limitation, aspirin, bandages, salves, or creams. In such an implementation, the information may further include a type of sample, or category thereof, for which a sample transaction payment card is valid. By way of example and not limitation, the electronic voucher may be valid for a sample of all OTC pain relievers made by a particular manufacturer. Alternatively, the electronic voucher may be valid for a specific OTC pain reliever made by the manufacturer.

In certain implementations, the information also includes a prescription for a prescription medication. In such implementations, an image may be stored on sample transaction payment card 102 which includes the signature of healthcare provider 108. In certain implementations, the image may contain other information required in specific jurisdictions for a pharmacist to dispense a prescription medical supply. Such information, by way of example and not limitation, may include an image of the written prescription in the handwriting of the prescribing healthcare provider, the name of the patient, dosing instructions, and/or the refill amount. In certain implementations, the image may be of the free sample.

In such an implementation where a prescription is included, the electronic voucher may be for a sample of a medication not usually stocked at the pharmacy in sufficient amounts to completely fulfill a prescription. In other such implementations, the electronic voucher may be for a sample of a name-brand medication while the prescription may be for the generic equivalent.

In certain implementations, card read-write device 116 stores additional information on sample transaction payment card 102. Wherein the electronic voucher is for a sample of a prescription medication, card read-write device 116 may additionally store, by way of example and not limitation, identifiers for the prescribing healthcare provider 108, the patient, and the prescription medication for which a sample is to be provided.

In certain implementations, card read-write device 116 is a memory card reader-writer. In such an implementation, sample transaction payment card 102 is a smart card and the account identifier and any additional information is stored in the memory of an embedded chip. In certain implementations, sample transaction payment card 102 is a contact smart card having a contact area that when inserted into card read-write device 116 makes contact with electrical connectors capable of writing the information to memory. In certain implementations, sample transaction payment card 102 is a contactless smart card in which the chip communicates with card read-write device 116 through radio-frequency identification (RFID) induction technology.

In certain implementations, card read-write device 116 is a magnetic card reader. In such an implementation, sample transaction payment card 102 has a magnetic data stripe. The account identifier and any additional information is stored on sample transaction payment card 102 when the magnetic data stripe is placed in physical contact with a read-write head of card read-write device 116. In certain implementations, sample transaction payment card 102 includes both an embedded chip and a magnetic stripe.

In one implementation, sample transaction payment card 102 may also include an image 112 printed on a surface. Image 112 may be preprinted on sample transaction payment card 102 by the pharmaceutical company and may serve as an advertisement. Alternatively, image 112 may be printed by the card processor and may relate to the medication prescribed by healthcare provider 108 or the free sample. Further, sample transaction payment card 102 may display a flat or raised account number as well as the prescription name, quantity, instructions, patient name, prescribing healthcare provider's name, and any other relevant information.

Wherein the card processor system is capable of printing image 112 on sample transaction payment card 102, the device may include a card printer such as, for example, the Direct-to-Card (DTC) 450 or High Definition Printing (HDP) 5000 commercially available from Fargo Electronics, Inc., a corporation located in Eden Prairie, Minn.

In certain implementations, association of the electronic voucher with sample transaction payment card 102 further involves using the card processor system to provide an identifier of a sponsor account that will cover the cost of the sample and that is to be associated with sample transaction payment card 102. The card processor system also provides information regarding the electronic voucher selected by healthcare provider 108 for storage on sample transaction payment card 102 to be provided to a transaction handler, such as one or more of the transaction handler (th) 502 (FIG. 5), wherein the account identifier and the information is stored in a database. In such an implementation, the database may be used to verify the authenticity of an electronic voucher stored on a consumer payment device presented at a merchant's location for redemption of a sample.

Figure 2:
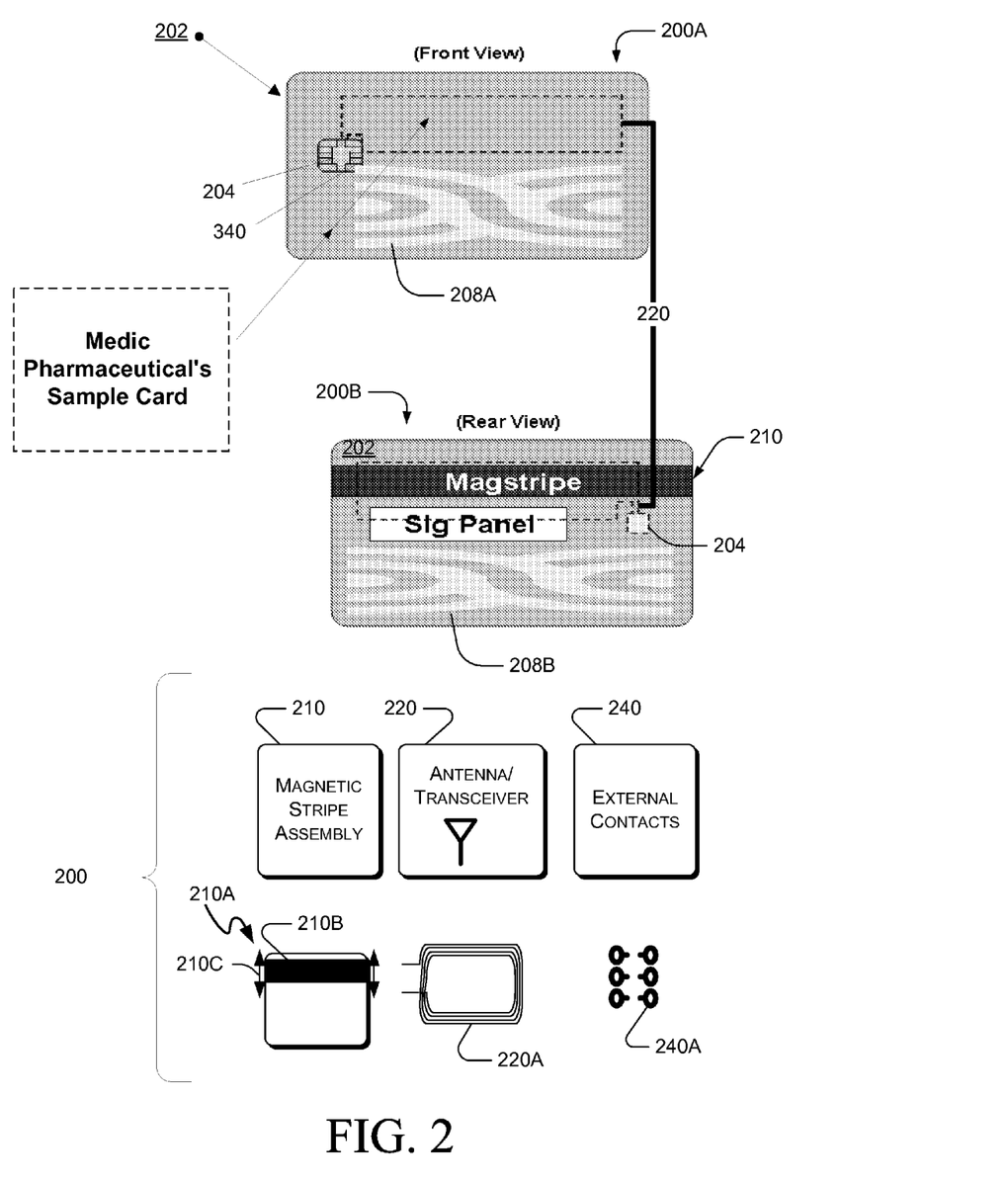
FIG. 2 illustrates possible alternative implementations of the data encoding area of a sample transaction payment card.

Turning to FIG. 2, both a front view 200A and a rear view 200B of an exemplary sample transaction payment card 202 are presented. Images may be displayed on both sides of sample transaction payment card 202, with image 208A on the front view 200A being either the same as or different from image 208B on the rear view 200B. In this illustration, the front view 200A also displays information about the provider of sample transaction payment card 202.

FIG. 2 also shows exemplary implementations of a data encoding area of sample transaction payment card 202. The data encoding area may include an optional shielding element, which allows desired electromagnetic, optical, or radiative signals to penetrate while protecting the data encoding area from physical abuse or damage. Sample transaction payment card 202 may optionally have areas outside of the data encoding area shielded from physical abuse or otherwise acceptable forms of electromagnetic radiation. Some of the acceptable signals that are allowed to penetrate the shielding and may include, but are not limited to, signals accompanying a magnetic field, RFID signals, IrDA signals, visible light, invisible light, modulated laser, and/or modulated RF communication signals. By way of example and not limitation, a selective shielding element may comprise a clear plastic shield, conformal coatings, an opaque plastic shield, or a clear thin film, depending on the implementation of the data encoding area.

Non-limiting examples of the data encoding area are shown at reference numeral 200, and include a magnetic stripe assembly 210, an antenna and/or transceiver 220, and electrical contacts 240. Magnetic stripe assembly 210 may comprise, in the implementation shown as 210A, a reprogrammable magnetic stripe assembly 210B that accepts data and/or commands from a processor and formats and renders that data into a form on a magnetic stripe that is readable by conventional merchant magnetic stripe-reading point of sale (POS) terminals. In this manner, the processor may program a particular account for use in a transaction as a function of user input selecting the account. Alternatively, the processor may erase the magnetic stripe of assembly 210, rendering the card useless in the event of its loss or theft. In the implementation shown as 210A, magnetic stripe assembly 210B at least partially slidably moves 210C into and out of an assembly of sample transaction payment card 202 (partial view shown), allowing sample transaction payment card 202 to conduct a transaction at a point of sale terminal that includes a magnetic stripe reader.

Continuing with FIG. 2, another implementation of the data encoding area is shown as an antenna and/or transceiver 220. Antenna and/or transceiver 220 may include commonly used loop inductors such as the one shown 220A or in those shown in related ISO standards for RF-readable smart cards. With such an interface, account data may be translated, modulated and transmitted in a manner acceptable by an RF contactless merchant POS terminal, an 802.11 WiFi or WiMax network, or by a cellular or RF communications network. For instance, antenna and/or transceiver 220 may receive a wireless communication from a card read-write device, where the wireless communication carries data for a sponsor's electronic voucher account that is to be written in memory to the data encoding area 200.

Electrical contacts 240 are yet another alternative implementation of the data encoding area shown in FIG. 2. With sample transaction payment card 202 possessing physical contacts such as an array of conductive pads or shapes 240A, sample transaction payment card 202 may be placed in physical contact with merchant POS terminals, and electrical contacts 240 may establish connectivity between imbedded integrated circuit 204 and the merchant's financial processing system. The processor may relay account-related information to the merchant POS terminal through the contact interface, thereby allowing sample transaction payment card 202 to be utilized with the large number of preexisting merchant POS terminals.

Figure 3:
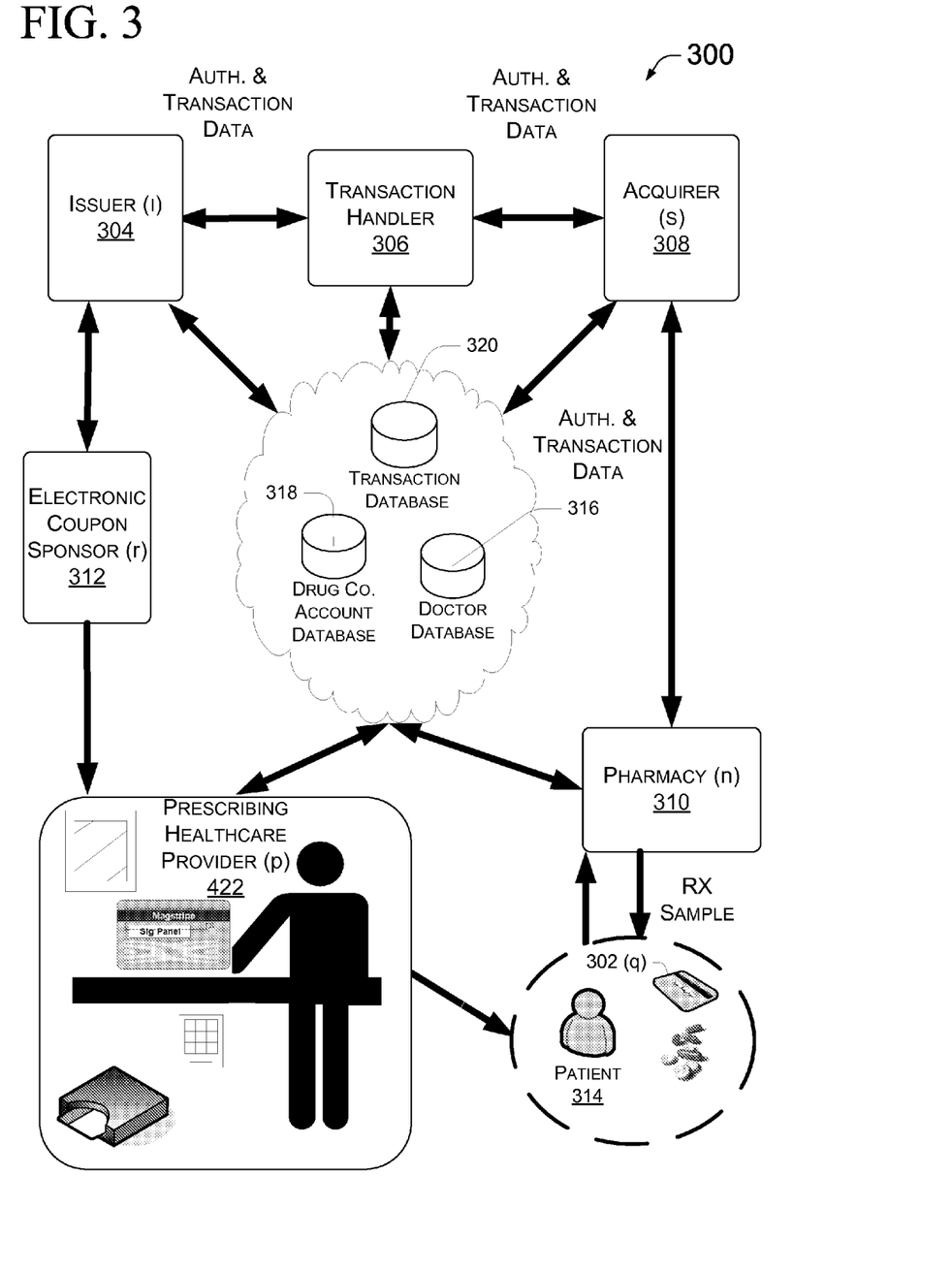
FIG. 3 depicts the environment within FIG. 5 where a sample transaction payment card is used by a patient to obtain a sample.

Within the exemplary payment processing system depicted in FIG. 5 and described below, FIG. 3 illustrates the general environment wherein a sample transaction payment card, such as sample transaction payment card 202 (FIG. 2) obtained by the environment described in connection with FIG. 1, is used by a patient 314 to receive a sample prescription or medical item from a merchant, such as a pharmacy (n) 310, that had been prescribed by a prescribing healthcare provider (p) 322 to patient 314. To start, at the POS terminal of pharmacy 310, patient 314 presents to Pharmacy 310 sample transaction payment card (q) 302. Pharmacy 310 uses a card reader associated with the POS terminal to read the information stored on sample transaction payment card 302, including the account identifier associated with the one or more electronic vouchers being sponsored, respectively, by one or more sponsors 312 (one such sponsor is indicated in FIG. 3 as sponsor (r) 312). In certain implementations, sample transaction payment card 302 is read by swiping sample transaction payment card 302 through the POS terminal to read data magnetically encoded in its magnetic stripe. In other implementations, the POS terminal reads sample transaction payment card 302 using a contactless technology, such as RFID, when patient 314 is near the POS terminal. In yet other implementations, to be read, sample transaction payment card 302 is inserted into the POS terminal such that external contacts on sample transaction payment card 302 establish connectivity with the POS terminal.

In certain implementations, other information is also read from sample transaction payment card 302, such as, by way of example and not limitation, an expiration date, a sample type, or patient 314's name. In such implementations, the POS terminal may determine whether the electronic voucher is valid for the sample requested. This may occur, by way of example and not limitation, by comparing the current date with the expiration data of the electronic voucher.

In certain implementations, the POS terminal may be connected to a database storing information regarding prescriptions patient 314 has had filled at pharmacy 310 or any related pharmacy 310(*n*). In such an implementation, the database may be used to determine whether patient 314 is taking any other medication that may interacted with the sample to be distributed. Wherein the sample is of a controlled substance included on a schedule, such a database may additionally be used to force compliance with regulations promulgated by the United States Drug Enforcement Agency. In such implementations, the database may be used to verify that use of the electronic voucher would not allow patient 314 to receive more then the legally allowed limit. By way of example and not limitation, where the sample is for a medication listed on Schedule II, such as Methadone, Oxycodone, or Fentanyl, patients are limited to a thirty (30) day supply unless they meet a legal exception. Thus, the database may be used to determine whether distribution of the sample, alone or in combination with other samples or prescriptions, would give patient 314 more than a thirty (30) day supply. Further, the prescription date may be checked against the date on which patient 314 is requesting the sample to ensure that the sample is being distributed within the legally allowed time frame from the prescription date. Alternatively, wherein the medication is restricted by the number of refills which may be distributed within a given time frame, such as medications on Schedule III and Schedule IV, the data base may be used to determine whether distribution of the sample may be considered a "refill" exceeding the allowed amount under law during that timeframe.

In certain implementations, patient 314 is requested to present identification. In such an implementation, the identification may be checked against a patient identifier read from sample transaction payment card 302 in order to verify that patient 314 was the same patient who was given sample transaction payment card 302 from healthcare provider 322. Alternatively, the identification may be used to verify that the individual presenting sample transaction payment card 302 is authorized to receive medication on behalf of patient 314, such as in the case of a parent or spouse of patient 314.

Upon receipt of sample transaction payment card 302, the transaction is processed similarly to the method to be described in connection with FIG. 5. Pharmacy 310 submits an authorization request to acquirer 308, which includes the account identifier read from sample transaction payment card 302.

In certain implementations, the authorization request is for only some of the samples or amounts described by the electronic voucher associated with the account identifier of sample transaction payment card 302. In such an implementation, pharmacy 310 can send the authorization request only for the types of medications or the amount of medication the pharmacy is capable of distributing at that time. In such a situation, patient 314 could then use the card at another pharmacy to receive the rest of the sample associated with the account identifier of the card. In such cases, memory of card 302 will be accordingly updated to reflect the progressive partial and complete filling of a prescription dispensed by each respective pharmacist (n) 310 to patient 314.

In certain implementations, the authorization request may additionally include a different account identifier that is separately supplied by the patient 314 (or agent thereof), where patient 314 intends to pay for the portion of the transaction with the pharmacist (n) 310 that is not free, and where that portion of the purchase is to be paid for by the patent's use of their personal credit card, debit card, personal check written on a checking account, or other portable consumer transaction payment device.

Where acquirer 308 is not the same entity as the issuer of the account associated with the account identifier read from sample transaction payment card 302, acquirer 308 forwards the transaction information to a transaction handler 306, who in turn forwards it to issuer 304 to verify that the account associated with electronic voucher sponsor 312 contains sufficient funds to reimburse pharmacy 310 for the sample.

Upon receipt of a reply from issuer 304, transaction handler 306 forwards an authorization response to acquirer 308, who forwards it to pharmacy 310. Where the authorization response contains an approval of the use of the electronic voucher, patient 314 is given the associated sample free of charge.

In certain implementations, the authorization response is only a partial response. In such implementations, the authorization request may have included types of samples or amounts not associated with the account identifier of sample transaction payment card 302.

In certain implementations, pharmacy 310 invalidates or deletes the electronic voucher(s) stored on sample transaction payment card 302 once the sample has been provided to patient 314. In certain implementations, sample transaction payment card 302 may be a one-time use card. In such an implementation, pharmacy 310 may forgo returning sample transaction payment card 302 to patient 314. In certain implementations, sample transaction payment card 302 is deactivated only after all of the samples described in the sample information have been redeemed by patient 314. In such an implementation, patient 314 may fill only part of the sample at any given time or may receive portions of the samples from different pharmacies.

In other implementations, sample transaction payment card 302 may be a multiple use card and is therefore not deactivated. In such an implementation, sample transaction payment card 302 may be used to store subsequent electronic vouchers and therefore is returned to patient 314. Alternatively, sample transaction payment card 302 may also be a credit card, debit card, or other form of a portable consumer device that can be used to conduct transactions for goods or services with merchants.

In certain implementations, approval of the transaction may be more involved. In such implementations, the authorization request includes additional information, by way of example and not limitation, the sample medication to be distributed, the prescribing healthcare provider, and/or the sponsor of the electronic voucher. In one implementation, database 316 may be used to, by way of example and not limitation, to verify the number of samples authorized by electronic voucher sponsor 312 for distribution generally or for distribution by a specific doctor. In other implementations, database 316 may be used to verify the types of prescription medications or OTC healthcare items a healthcare provider may distribute using a sample transaction payment card. The number and type of samples distributed in the transaction may then be reflected against the amount and types the healthcare provider has available to distribute in the future.

In other implementations, database 318 is used. Database 318 may contain information regarding all sample transaction payment cards issued for distribution of each type of sample medication or healthcare item. By way of example and not limitation, database 318 may be used to verify the authenticity of sample transaction payment card 302 or that sample transaction payment card 302 has only been used once.

In yet another implementation, another database, database 320, contains information regarding all activated sample transaction payment cards, wherein prescribing healthcare provider 322 activates sample transaction payment card 302 prior to giving it to patient 314. Alternatively, a representative of electronic voucher sponsor 312 may activate sample transaction payment card 302 prior to providing it to healthcare provider 322. Approval of the transaction request may, in such an implementation, depend upon verification that sample transaction payment card 302 is activated.

Once the authorization request is approved and the sample associated with the electronic voucher stored on sample transaction payment card 302 is distributed, pharmacy 310 may submit a payment request to payment processing system 300 for reimbursement from electronic voucher sponsor 312's account for the cost of the sample. Specifically, pharmacy 310 submits a request for payment to acquirer 308. Where acquirer 308 is not the same entity as the issuer of the account associated with the account identifier stored on sample transaction payment card 302, acquirer 308 forwards the request to transaction handler 306. Transaction handler 306 in turn requests payment for the sample from issuer 304, where issuer 304 is the issuer of the account associated with electronic voucher sponsor 312. Issuer 304 debits the account and forwards the payment to transaction handler 306 who forwards the payment to acquirer 308. Finally, acquirer 308 credits the account of pharmacy 310 for the cost of the distributed sample.

As will be understood by a person of ordinary skill in the art, the process described in connection with FIG. 3 is equally applicable to the situation where a patient uses a sample transaction payment card having multiple electronic vouchers stored thereon to receive several different samples. In such a situation, the electronic vouchers may be provided by different electronic voucher sponsors (i.e., sponsor (r) 312, sponsor (r+1) 312, sponsor (r+2) 312, etc.) having accounts issued by different issuers for the purpose of reimbursing each dispensing pharmacist (n) 310 for samples. Further, it will be clear to a person of ordinary skill in the art that a sample transaction payment card may have multiple electronic vouchers stored thereon that are valid at different pharmacies, each pharmacy having a different acquirer.

Figure 4:
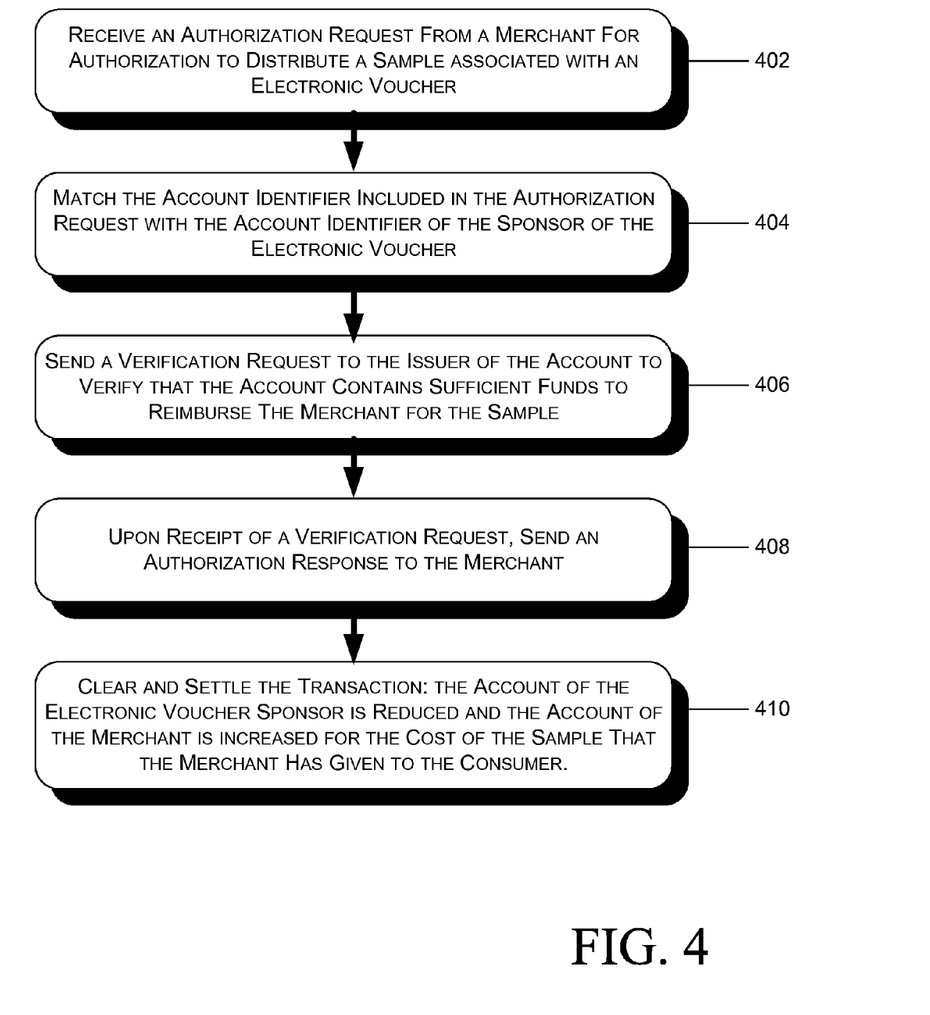
FIG. 4 depicts a flow chart of an exemplary method used by a transaction handler to process an electronic voucher stored on a sample transaction payment card.

Turning now to FIG. 4, a flow chart of an exemplary method used by a transaction handler to process an electronic voucher stored on a consumer payment device is presented. As indicated by block 402, the transaction handler receives an authorization request from a merchant (e.g., via the merchant's acquirer), requesting authorization to distribute a sample associated with an electronic voucher to a patient. Upon receipt of the request, the transaction handler matches the account identifier included in the request with the account identifier associated with the electronic voucher sponsor, as indicated by block 404. In certain implementations, if the account identifier included in the request does not match the account identifier associated with the electronic voucher sponsor, the transaction handler sends an authorization response to the merchant indicating that the transaction is not authorized such that there will be a denial of the distribution of the free sample to the patient. In such an implementation, the process may end.

In the illustrated implementation of FIG. 4, the transaction handler next sends a request to the issuer of the account associated with the electronic voucher sponsor requesting verification that the account contains sufficient funds to reimburse the merchant for the sample, as indicated by block 406. As indicated by block 408, upon receipt of a response from the issuer, the transaction handler sends a response to the merchant. Where the issuer confirms that the account contains sufficient funds, the authorization request may contain an approval. Finally, as indicated by block 410, the transaction handler clears and settles the transaction by facilitating a process in which the issuer debits the account of the electronic voucher sponsor and an acquirer for the pharmacist credits the pharmacist's account for the cost of the free prescription medical supply sample that the pharmacist compounded and dispensed to the patient.

In certain implementations, individual blocks described above may be combined, eliminated, or reordered.

In certain implementations, instructions are encoded in computer readable medium wherein those instructions are executed by a processor to perform one or more of the blocks 402, 404, 406, 408, and 410 recited in FIG. 4.

In certain implementations, individual steps described above in relation to FIG. 4 may be combined, eliminated, or reordered. In yet other implementations, instructions reside in any other computer program product, where those instructions are executed by a computer external to, or internal to, a computing system to perform one or more of the blocks 402, 404, 406, 408, and 410 recited in FIG. 4. In either case the instructions may be encoded in a computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

An Exemplary Transaction Processing System

Figure 5:
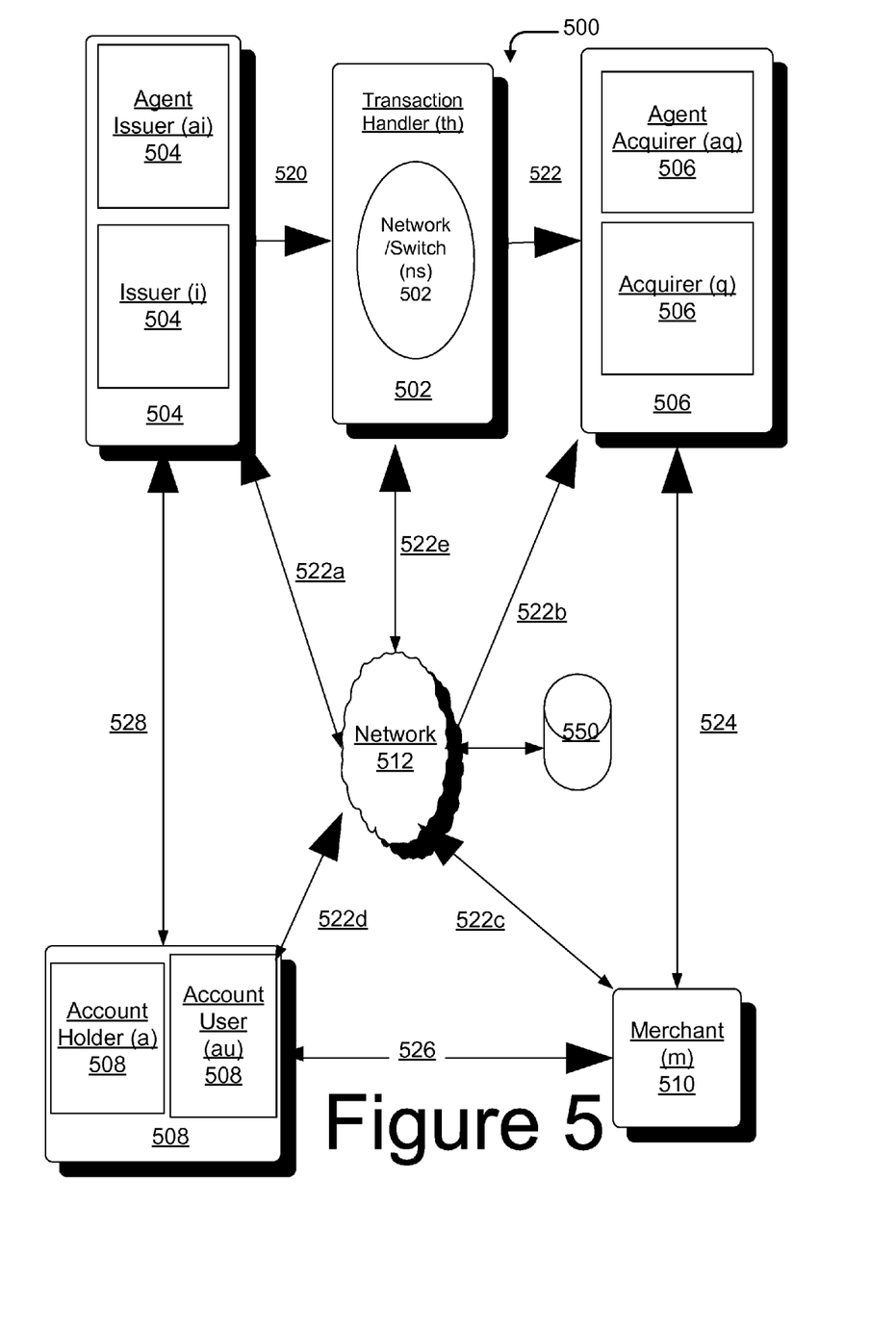
FIG. 5 illustrates an exemplary payment processing network, depicting the general environment where a sample transaction payment card may be used by a card holder to obtain a sample.

Referring to FIG. 5, a transaction processing system 500 is seen. The general environment of FIG. 5 include that of a merchant (m) 510, such as the merchant, who can conduct a transaction for goods and/or services with an account user (au) (e.g., consumer) on an account issued to an account holder (a) 508 by an issuer (i) 504, where the processes of paying and being paid for the transaction are coordinated by at least one transaction handler (th) 502 (e.g., the transaction handler) (collectively "users"). The transaction includes participation from different entities that are each a component of the transaction processing system 500.

The transaction processing system 500 may have at least one of a plurality of transaction handlers (th) 502 that includes transaction handler (l) 502 through transaction handler (TH) 502, where TH can be up to and greater than an eight digit integer.

The transaction processing system 500 has a plurality of merchants (m) 510 that includes merchant (l) 510 through merchant (M) 510, where M can be up to and greater than an eight digit integer. Merchant (m) 510 may be a person or entity that sells goods and/or services. Merchant (m) 510 may also be, for instance, a manufacturer, a distributor, a retailer, a load agent, a drugstore, a grocery store, a gas station, a hardware store, a supermarket, a boutique, a restaurant, or a doctor's office. In a business-to-business setting, the account holder (a) 508 may be a second merchant (m) 510 making a purchase from another merchant (m) 510.

Transaction processing system 500 includes account user (l) 508 through account user (AU) 508, where AU can be as large as a ten digit integer or larger. Each account user (au) conducts a transaction with merchant (m) 510 for goods and/or services using the account that has been issued by an issuer (i) 504 to a corresponding account holder (a) 508. Data from the transaction on the account is collected by the merchant (m) 510 and forwarded to a corresponding acquirer (a) 506. Acquirer (a) 506 forwards the data to transaction handler (th)

502 who facilitates payment for the transaction from the account issued by the issuer (i) 504 to account holder (a) 508.

Transaction processing system 500 has a plurality of acquirers (q) 506. Each acquirer (q) 506 may be assisted in processing one or more transactions by a corresponding agent acquirer (aq) 506, where 'q' can be an integer from 1 to Q, where aq can be an integer from 1 to AQ, and where Q and AQ can be as large as a eight digit integer or larger. Each acquirer (q) 506 may be assisted in processing one or more transactions by a corresponding agent acquirer (aq) 506, where 'q' can be an integer from 1 to Q, where aq can be an integer from 1 to AQ, and where Q and AQ can be as large as a eight digit integer or larger.

The transaction handler (th) 502 may process a plurality of transactions within the transaction processing system 500. The transaction handler (th) 502 can include one or a plurality or networks and switches (ns) 502. Each network/switch (ns) 502 can be a mainframe computer in a geographic location different than each other network/switch (ns) 502, where 'ns' is an integer from one to NS, and where NS can be as large as a four digit integer or larger.

Dedicated communication systems 520, 522 (e.g., private communication network(s)) facilitate communication between the transaction handler (th) 502 and each issuer (i) 504 and each acquirer (a) 506. A Network 512, via e-mail, the World Wide Web, cellular telephony, and/or other optionally public and private communications systems, can facilitate communications 522a-522e among and between each issuer (i) 504, each acquirer (a) 506, each merchant (m) 510, each account holder (a) 508, and the transaction handler (th) 502. Alternatively and optionally, one or more dedicated communication systems 524, 526, and 528 can facilitate respective communications between each acquirer (a) 506 and each merchant (m) 510, each merchant (m) and each account holder (a) 508, and each account holder (a) 508 and each issuer (i) 504, respectively.

The Network 512 may represent any of a variety of suitable means for exchanging data, such as: an Internet, an intranet, an extranet, a wide area network (WAN), a local area network (LAN), a virtual private network, a satellite communications network, an Automatic Teller Machine (ATM) network, an interactive television network, or any combination of the forgoing. Network 512 may contain either or both wired and wireless connections for the transmission of signals including electrical, magnetic, and a combination thereof. Examples of such connections are known in the art and include: radio frequency connections, optical connections, etc. To illustrate, the connection for the transmission of signals may be a telephone link, a Digital Subscriber Line, or cable link. Moreover, network 512 may utilize any of a variety of communication protocols, such as Transmission Control Protocol/Internet Protocol (TCP/IP), for example. There may be multiple nodes within the network 512, each of which may conduct some level of processing on the data transmitted within the transaction processing system 500.

Users of the transaction processing system 500 may interact with one another or receive data about one another within the transaction processing system 500 using any of a variety of communication devices. The communication device may have a processing unit operatively connected to a display and memory such as Random Access Memory ("RAM") and/or Read-Only Memory ("ROM"). The communication device may be combination of hardware and software that enables an input device such as a keyboard, a mouse, a stylus and touch screen, or the like.

For example, use of the transaction processing system 500 by the account holder (a) 508 may include the use of a portable consumer device (PCD), which can be an implementation of a portable prescription transaction payment device. The PCD may be one of the communication devices, or may be used in conjunction with, or as part of, the communication device. The PCD may be in a form factor that can be a card (e.g., bank card, payment card, financial card, credit card, charge card, debit card, gift card, transit pass, smart card, access card, a payroll card, security card, healthcare card, or telephone card), a tag, a wristwatch, wrist band, a key ring, a fob (e.g., SPEEDPASS® commercially available from ExxonMobil Corporation), a machine readable medium containing account information, a pager, a cellular telephone, a personal digital assistant, a digital audio player, a computer (e.g., laptop computer), a set-top box, a portable workstation, a minicomputer, or a combination thereof. The PCD may have near field or far field communication capabilities (e.g., satellite communication or communication to cell sites of a cellular network) for telephony or data transfer such as communication with a global positioning system (GPS). The PCD may support a number of services such as SMS for text messaging and Multimedia Messaging Service (MMS) for transfer of photographs and videos, electronic mail (email) access.

The PCD may include a computer readable medium. The computer readable medium, such as a magnetic stripe or a memory of a chip or a chipset, may include a volatile, a non-volatile, a read only, or a programmable memory that stores data, such as an account identifier, a consumer identifier, and/or an expiration date. The computer readable medium may including executable instructions that, when executed by a computer, the computer will perform a method. For example, the computer readable memory may include information such as the account number or an account holder (a) 508's name.

Examples of the PCD with memory and executable instructions include: a smart card, a personal digital assistant, a digital audio player, a cellular telephone, a personal computer, or a combination thereof. To illustrate, the PCD may be a financial card that can be used by a consumer to conduct a contactless transaction with a merchant, where the financial card includes a microprocessor, a programmable memory, and a transponder (e.g., transmitter or receiver). The financial card can have near field communication capabilities, such as by one or more radio frequency communications such as are used in a "Blue Tooth" communication wireless protocol for exchanging data over short distances from fixed and mobile devices, thereby creating personal area networks.

Merchant (m) 510 may utilize at least one POI terminal (e.g., Point of Service or browser enabled consumer cellular telephone); that can communicate with the account user (au) 508, the acquirer (a) 506, the transaction handler (th) 502, or the issuer (i) 504. A Point of Interaction (POI) can be a physical or virtual communication vehicle that provides the opportunity, through any channel to engage with the consumer for the purposes of providing content, messaging or other communication, related directly or indirectly to the facilitation or execution of a transaction between the merchant (m) 510 and the consumer. Examples of the POI include: a physical or virtual Point of Service (POS) terminal, the PCD of the consumer, a portable digital assistant, a cellular telephone, paper mail, e-mail, an Internet website rendered via a browser executing on computing device, or a combination of the forgoing. Thus, the POI terminal is in operative communication with the transaction processing system 500.

The PCD may interface with the POI using a mechanism including any suitable electrical, magnetic, or optical interfacing system such as a contactless system using radio frequency, a magnetic field recognition system, or a contact system such as a magnetic stripe reader. To illustrate, the POI may have a magnetic stripe reader that makes contact with the magnetic stripe of a healthcare card (e.g., Flexible Savings Account card) of the consumer. As such, data encoded in the magnetic stripe on the healthcare card of consumer read and passed to the POI at merchant (m) 510. These data can include an account identifier of a healthcare account. In another example, the POI may be the PCD of the consumer, such as the cellular telephone of the consumer, where the merchant (m) 510, or an agent thereof, receives the account identifier of the consumer via a webpage of an interactive website rendered by a browser executing on a World Wide Web (Web) enabled PCD.

Typically, a transaction begins with account user (au) 508 presenting the portable consumer device to the merchant (m) 510 to initiate an exchange for resources (e.g., a good or service). The portable consumer device may be associated with an account (e.g., a credit account) of account holder (a) 508 that was issued to the account holder (a) 508 by issuer (i) 504.

Merchant (m) 510 may use the POI terminal to obtain account information, such as a number of the account of the account holder (a) 508, from the portable consumer device. The portable consumer device may interface with the POI terminal using a mechanism including any suitable electrical, magnetic, or optical interfacing system such as a contactless system using radio frequency or magnetic field recognition system or contact system such as a magnetic stripe reader. The POI terminal sends a transaction authorization request to the issuer (i) 504 of the account associated with the PCD. Alternatively, or in combination, the PCD may communicate with issuer (i) 504, transaction handler (th) 502, or acquirer (a) 506.

Issuer (i) 504 may authorize the transaction and forward same to the transaction handler (th) 502. Transaction handler (th) 502 may also clear the transaction. Authorization includes issuer (i) 504, or transaction handler (th) 502 on behalf of issuer (i) 504, authorizing the transaction in connection with issuer (i) 504's instructions such as through the use of business rules. The business rules could include instructions or guidelines from the transaction handler (th) 502, the account holder (a) 508, the merchant (m) 510, the acquirer (a) 506, the issuer (i) 504, a related financial institution, or combinations thereof. The transaction handler (th) 502 may, but need not, maintain a log or history of authorized transactions. Once approved, the merchant (m) 510 may record the authorization, allowing the account user (au) 508 to receive the good or service from merchant (m) or an agent thereof.

The merchant (m) 510 may, at discrete periods, such as the end of the day, submit a list of authorized transactions to the acquirer (a) 506 or other transaction related data for processing through the transaction processing system 500. The transaction handler (th) 502 may optionally compare the submitted authorized transaction list with its own log of authorized transactions. The transaction handler (th) 502 may route authorization transaction amount requests from the corresponding acquirer (a) 506 to the corresponding issuer (i) 504 involved in each transaction. Once the acquirer (a) 506 receives the payment of the authorized transaction from the issuer (i) 504, the acquirer (a) 506 can forward the payment to the merchant (m) 510 less any transaction costs, such as fees for the processing of the transaction. If the transaction involves a debit or pre-paid card, the acquirer (a) 506 may choose not to wait for the issuer (i) 504 to forward the payment prior to paying merchant (m) 510.

There may be intermittent steps in the foregoing process, some of which may occur simultaneously. For example, the acquirer (a) 506 can initiate the clearing and settling process, which can result in payment to the acquirer (a) 506 for the amount of the transaction. The acquirer (a) 506 may request from the transaction handler (th) 502 that the transaction be cleared and settled. Clearing includes the exchange of financial information between the issuer (i) 504 and the acquirer (a) 506 and settlement includes the exchange of funds. The transaction handler (th) 502 can provide services in connection with settlement of the transaction. The settlement of a transaction includes depositing an amount of the transaction settlement from a settlement house, such as a settlement bank, which transaction handler (th) 502 typically chooses, into a clearinghouse bank, such as a clearing bank, that acquirer (a) 506 typically chooses. The issuer (i) 504 deposits the same from a clearinghouse bank, such as a clearing bank, which the issuer (i) 504 typically chooses, into the settlement house. Thus, a typical transaction involves various entities to request, authorize, and fulfill processing the transaction.

The transaction processing system 500 will preferably have network components suitable for scaling the number and data payload size of transactions that can be authorized, cleared and settled in both real time and batch processing. These include hardware, software, data elements, and storage network devices for the same. Examples of transaction processing system 500 include those operated, at least in part, by: American Express Travel Related Services Company, Inc; MasterCard International, Inc.; Discover Financial Services, Inc.; First Data Corporation; Diners Club International, LTD; Visa Inc.; and agents of the foregoing.

Each of the network/switch (ns) 502 can include one or more data centers for processing transactions, where each transaction can include up to 100 kilobytes of data or more. The data corresponding to the transaction can include information about the types and quantities of goods and services in the transaction, information about the account holder (a) 508, the account user (au) 508, the merchant (m) 510, tax and incentive treatment(s) of the goods and services, coupons, rebates, rewards, loyalty, discounts, returns, exchanges, cash-back transactions, etc.

By way of example, network/switch (ns) 502 can include one or more mainframe computers (e.g., one or more IBM mainframe computers) for one or more server farms (e.g., one or more Sun UNIX Super servers), where the mainframe computers and server farms can be in diverse geographic locations.

Each issuer (i) 504 (or agent issuer (ai) 504 thereof) and each acquirer (a) 506 (or agent acquirer (aq) 506 thereof) can use or more router/switch (e.g., Cisco™ routers/switches) to communicate with each network/switch (ns) 502 via dedicated communication systems.

Transaction handler (th) 502 can store information about transactions processed through transaction processing system 500 in data warehouses such as may be incorporated as part of the plurality of networks/switches 502. This information can be data mined. The data mining transaction research and modeling can be used for advertising, account holder and merchant loyalty incentives and rewards, fraud detection and prediction, and to develop tools to demonstrate savings and efficiencies made possible by use of the transaction processing system 500 over paying and being paid by cash, or other traditional payment mechanisms.

The VisaNet® system is an example component of the transaction handler (th) 502 in the transaction processing system 500. Presently, the VisaNet® system is operated in part by Visa Inc. As of 2006, the VisaNet® system Inc. was processing around 300 million transaction daily, on over 1 billion accounts used in over 170 countries. Financial instructions numbering over 16,000 connected through the VisaNet® system to around 20 million merchants (m) 510. In 2007, around 71 billion transactions for about 4 trillion U.S. dollars were cleared and settled through the VisaNet® system, some of which involved a communication length of around 24,000 miles in around two (2) seconds.

The following example is presented to further illustrate to persons skilled in the art how to make and use the invention. This example is not intended as a limitation, however, upon the scope of the invention, which is defined only by the appended claims.

EXAMPLE

By way of example and not limitation, a doctor may diagnose a patient as needing a medication, manufactured and distributed by a given pharmaceutical company, and decide to provide a sample using a sample transaction payment card according to the present discussion. Through use of a card processor system, the doctor can determine whether he or she has available samples of the medications to distribute and, if so, can request that a sample transaction payment card be activated and associated with an electronic voucher for a sample of the medication. The request may include a specific number of samples for distribution and a coupon for an OTC item. The request, for example, may be received by an sponsor account issuer and/or a transaction handler who will facilitate the activation of the sample transaction payment card and association of account identifier with the sample drug and/or medical supply information. Here, the account holder of the sponsor account might be a pharmaceutical company who wishes to promote the use of the drug by giving out free samples to patients via their prescribing physicians.

The prescribing doctor, or agent thereof, may additionally use the card processor system to store information relating to the sample medications, the prescribing doctor him or herself, the patient, prescriptions, dosing instructions, and any other information on the sample transaction payment card. These data could be stored via a magnetic stripe, imbedded microchip, or other memory storage device.

Once done, the patient then presents the sample transaction payment card to a pharmacy to redeem the samples. The pharmacy may require the patient to show identification, such as a driver's license, to compare with information printed or stored on the sample transaction payment card. The pharmacy then sends an authorization request for permission to dispense the medication and to charge the pharmaceutical company's account. The authorization request is, for example, received by the pharmacy's acquirer who forwards it for processing by a transaction handler.

The transaction handler may then send an authorization response authorizing the distribution of the samples after matching the account identifier of the sample transaction payment card activated by the doctor with the account identifier of the card presented to the pharmacy. Upon receiving the authorization response, the pharmacy may then distribute the approved quantity of the medication to the patient. If the sample transaction payment card is a one-time use card, the transaction handler may additionally deactivate it. The transaction handler may also send a request to the issuer of the sample transaction payment card to debit the pharmaceutical company's account for the cost of the samples and forward that payment to the acquirer for deposit in the pharmacy's account.

The steps, methods, processes, and devices described in connection with the implementations disclosed herein, are made with reference to the Figures, in which like numerals represent the same or similar elements. While described in terms of the best mode, it will be appreciated by those skilled in the art that the description is intended to cover alternatives, modifications, and equivalents as may be included within the spirit and scope of the invention as defined by the appended claims and their equivalents as supported by the following disclosure and drawings. Reference throughout this specification to "one implementation," "an implementation," or similar language means that a particular feature, structure, or characteristic described in connection with the implementation is included in at least one implementation of the present invention. Thus, appearances of the phrases "in one implementation," "in an implementation," and similar language throughout this specification may, but do not necessarily, all refer to the same implementation.

The described features, structures, or characteristics of the invention may be combined in any suitable manner in one or more implementations. In the following description, numerous specific details are recited to provide a thorough understanding of implementations of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one implementation of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A portable prescription sample transaction payment device comprising:
   a substrate having surface with an image rendering thereon that corresponds to a prescription medical supply sample;
   and
   memory, in contact with the substrate, having data encoded therein including:
   an identifier for the prescription medical supply sample;
   a quantity for the prescription medical supply sample;
   a dosage for the prescription medical supply sample; and an identifier for a patient;

a pharmaceutical company account for a dispensing pharmacist to charge the cost of the prescription medical supply sample for payment to a dispensing pharmacist account to reimburse the dispensing pharmacist for the prescription medical supply sample;

an image corresponding to the prescription medical supply sample; and an identifier for a prescribing medical practitioner prescribing the prescription medical supply sample to the patient.

2. The portable prescription sample transaction payment device as defined in claim 1, wherein:

the pharmaceutical company account is a type of consumer account issued by an issuer to a pharmaceutical company;

the portable prescription sample transaction payment device is a type of a portable prescription sample transaction payment device that is associated with a consumer account for a consumer to engage in a plurality of transactions on the consumer account with a plurality of merchants in a payment processing network;

the payment processing network includes a plurality of merchants and consumers engaging in a plurality of transactions on a plurality of respective consumer accounts that respective issuers issue to the consumers; and each said transaction involves the merchant submitting the transaction to an acquirer for processing by a transaction handler who requests the issuer to obtain payment for the transaction from the consumer account, and wherein the issuer forwards the payment to the transaction handler who forwards the payment to the acquirer to reimburse the merchant for the transaction.

3. The portable prescription sample transaction payment device as defined in claim 1, wherein the data encoded in the memory further includes an image of a prescription for the patient from the prescribing medical practitioner.

4. The portable prescription sample transaction payment device as defined in claim 3, wherein the image of the prescription comprises respective images corresponding to:

the identifier for the patient;

the identifier for the prescribing medical practitioner of the prescription medical supply sample;

the identifier for the prescription medical supply sample; and the quantity of the prescription medical supply sample.

5. The portable prescription sample transaction payment device as defined in claim 1, wherein the image corresponding to the prescription medical supply sample includes a code identifying the prescription medical supply sample and configured for being scanned by a scanner at a Point of Service terminal.

6. The portable prescription sample transaction payment device as defined in claim 1, wherein the image corresponding to the prescription medical supply sample includes an advertisement selected from the group consisting of:

an advertisement for the prescription medical supply sample;

an advertisement not for the prescription medical supply sample;

an advertisement for the dispensing pharmacist;

an advertisement for a different product other than the prescription medical supply sample that is also provided by the dispensing pharmacist; and a combination of the foregoing.

7. The portable prescription sample transaction payment device as defined in claim 1, wherein the image corresponding to the prescription medical supply sample includes an advertisement selected from the group consisting of:

an advertisement for a merchant geographically proximal to the prescribing medical practitioner;

an advertisement for a merchant geographically proximal to the dispensing pharmacist; and a combination of the foregoing.

8. The portable prescription sample transaction payment device as defined in claim 1, wherein the memory of the portable prescription sample transaction payment device is selected from the group consisting of:

a non-volatile memory of a semiconductor device;

a magnetic encoded data region of a magnetic stripe; and a combination of the foregoing.

9. The portable prescription sample transaction payment device as defined in claim 1, wherein the substrate is a portion of a consumer transaction payment card selected from the group consisting of:

a smart card having a Radio Frequency Identification (RFID) tag, a transponder device and a microchip; and a magstripe card; and a combination of the foregoing.

10. The portable prescription sample transaction payment device as defined in claim 1, further comprising means for the memory to receive the information by a communication selected from the group consisting of a wireless communication, a hardwired communication, and a magnetic encoded communication for track data received by modifying the magnetism of magnetic particles on a band of magnetic material on the portable prescription sample transaction payment device.

11. The portable prescription sample transaction payment device as defined in claim 1, wherein data in the memory of the portable prescription sample transaction payment device further comprises an identifier, a quantity, and a dosage of a prescription medical supply, other than the prescription medical supply sample, being prescribed by the prescribing medical practitioner to the patient.

12. The portable prescription sample transaction payment device as defined in claim 11, wherein the identifier for the prescription medical supply sample and the identifier for the prescription medical supply, other than the prescription medical supply sample, are both selected from the group consisting of:

a Stock Keeping Unit (SKU);

a Universal Product Code (UPC);

a National Drug Code (NDC);

a trademark;

a commodity type and a trade name of a provider of the commodity type;

an active ingredient of the commodity type and the trade name of the provider of the commodity type; and a combination of the foregoing.

13. A portable prescription transaction payment device comprising:

memory, embedded in a substrate, having stored therein:

an identifier, quantity, and dosage for each of a plurality of:

a prescription medical supply sample prescribed by a prescribing medical practitioner to a patient; and a non-sample prescription medical supply each being prescribed by a corresponding said prescribing medical practitioner to the patient;

for each said prescription medical supply sample, a pharmaceutical company account for a dispensing pharmacist to charge the cost of the prescription medical supply sample for payment to a dispensing pharmacist account to reimburse the dispensing pharmacist for the prescription medical supply sample;

an identifier for the patient;

an identifier for each said prescribing medical practitioner;

an identifier for a consumer account issued by an issuer to the patient; and an identifier to correlate which said prescription for the patient was prescribed by which said prescribing medical practitioner, wherein:

the pharmaceutical company account and the consumer account are each an account in a payment processing network by which a consumer can engage in a plurality of transactions on the account with a plurality of merchants in the payment processing network;

the payment processing network includes a plurality of said merchants and said consumers engaging in the plurality of said transactions on a plurality of respective said accounts that respective said issuers issue to the consumers; and each said transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction;

and means for providing access to the information in the memory.

14. The portable prescription transaction payment device as defined in claim 13, wherein the consumer account issued by the issuer to the patient is a type selected from the group consisting of a Flexible Savings Account (FSA), a Health Savings Account (HAS), or a Health Reimbursement Account (HRA).

15. The portable prescription transaction payment device as defined in claim 13, wherein the substrate has an image in a surface that the includes representing at least a portion of the information in the memory for being read by the image being scanned by a scanner at a Point of Service terminal.

16. The portable prescription transaction payment device as defined in claim 13, wherein the memory is selected from the group consisting of:

a non-volatile memory of a semiconductor device;

a magnetic encoded data region of a magnetic stripe; and a combination of the foregoing.

17. The portable prescription transaction payment device as defined in claim 13, wherein the substrate is a portion of a consumer transaction payment card selected from the group consisting of:

a smart card having a Radio Frequency Identification (RFID) tag, a transponder device and a microchip; and a magstripe card; and a combination of the foregoing.

18. The portable prescription transaction payment device as defined in claim 13, wherein the information in the memory further includes an image of each said prescription for the patient that was prescribed by the corresponding said prescribing medical practitioner.

19. The portable prescription transaction payment device as defined in claim 18, wherein, for each said image of each said prescription, the prescription in the image is hand written by the prescribing medical practitioner.

20. The portable prescription transaction payment device as defined in claim 18, further comprising means for the memory to receive the information by a communication selected from the group consisting of a wireless communication, a hardwired communication, and a magnetic encoded communication for track data received by modifying the magnetism of magnetic particles on a band of magnetic material on the portable prescription sample transaction payment device.

21. The portable prescription transaction payment device as defined in claim 20, wherein, for each said image of each said prescription, the identifier for the prescribing medical practitioner comprises a handwritten signature of the prescribing medical practitioner.

22. The portable prescription transaction payment device as defined in claim 18, wherein each said image of each said prescription comprises respective images corresponding to:

the identifier for the patient;

the identifier for the prescribing medical practitioner; and the identifier, quantity, and dosage identifier for the prescription medical supply sample; and the identifier, quantity, and dosage identifier for the non-sample prescription medical supply.

23. A portable prescription transaction payment device comprising:

memory, embedded in a substrate, having information stored therein, wherein:

the substrate has an image on a surface thereof that includes a representation of at least a portion of the information in the memory for being read by the image being scanned by a scanner at a Point of Service terminal:

the information includes:

an identifier, quantity, and dosage for each of a plurality of:

a prescription medical supply sample prescribed by a prescribing medical practitioner to a patient; and a non-sample prescription medical supply prescribed by a corresponding said prescribing medical practitioner to the patient;

an image, having multiple portion, of each said prescription for the patient that was prescribed by the corresponding said prescribing medical practitioner, wherein the portions of the image correspond to:

the identifier for the patient;

the identifier for the prescribing medical practitioner; and the identifier, quantity, and dosage identifier for the prescription medical supply sample; and the identifier, quantity, and dosage identifier for the non-sample prescription medical supply;

for each said prescription medical supply sample, a pharmaceutical company account for a dispensing pharmacist to charge the cost of the prescription medical supply sample for payment to a dispensing pharmacist account to reimburse the dispensing pharmacist for the prescription medical supply sample; and an identifier to correlate which said prescription for the patient was prescribed by which said prescribing medical practitioner, wherein:

the pharmaceutical company account and the consumer account are each an account in a payment processing network by which a consumer can engage in a plurality of transactions on the account with a plurality of merchants in the payment processing network;

the payment processing network includes a plurality of said merchants and said consumers engaging in the plurality of said transactions on a plurality of respective said accounts that respective said issuers issue to the consumers; and each said transaction involves the merchant submitting the transaction to an acquirer for processing by a transaction handler who requests the issuer to obtain payment for the transaction from the account, wherein the issuer forwards the payment to the transaction handler who forwards the payment to the acquirer to reimburse the merchant for the transaction;

and means for providing access to the information in the memory.

24. The portable prescription transaction payment device as defined in claim 23, wherein the memory is selected from the group consisting of:

a non-volatile memory of a semiconductor device;

a magnetic encoded data region of a magnetic stripe; and a combination of the foregoing.

25. The portable prescription transaction payment device as defined in claim 23, wherein the substrate is a portion of a consumer transaction payment card selected from the group consisting of:

a smart card having a Radio Frequency Identification (RFID) tag, a transponder device and a microchip; and a magstripe card; and a combination of the foregoing.

26. The portable prescription transaction payment device as defined in claim 23, further comprising means for the memory to receive the information by a communication selected from the group consisting of a wireless communication, a hardwired communication, and a magnetic encoded communication for track data received by modifying the magnetism of magnetic particles on a band of magnetic material on the portable prescription sample transaction payment device.

27. The portable prescription transaction payment device as defined in claim 23, wherein, for each said image of each said prescription, the identifier for the prescribing medical practitioner comprises a handwritten signature of the prescribing medical practitioner.

28. The portable prescription transaction payment device as defined in claim 23, wherein, for each said image of each said prescription, the prescription in the image is hand written by the prescribing medical practitioner.

* * * * *